United States Patent [19]

Nafziger et al.

[11] Patent Number: 4,996,351

[45] Date of Patent: Feb. 26, 1991

[54] PROCESS FOR REDUCING THE QUANTITY OF HYDROLYZABLE CHLORIDES IN ISOCYANATES

[75] Inventors: John L. Nafziger; Mark J. Hazelrigg, both of Lake Jackson, Tex.

[73] Assignee: The Dow Chemical Company, Midland, Mich.

[21] Appl. No.: 7,317

[22] Filed: Jan. 27, 1987

[51] Int. Cl.$^5$ ............................................. C07C 249/00
[52] U.S. Cl. ..................................................... 560/352
[58] Field of Search ......................................... 560/352

[56] References Cited

FOREIGN PATENT DOCUMENTS 1458747 12/1976 United Kingdom ................ 560/352

*Primary Examiner*—Alan Siegel
*Attorney, Agent, or Firm*—Carol J. Cavender

[57] ABSTRACT

This invention is a process for removing volatile impurities from a crude isocyanate compound which is prepared in the phosgenation of a primary amine, comprising heating said crude isocyanate compound to a temperature to volatilize said volatile impurities in the presence of an acidic material containing a plurality of strong acid groups. The process permits faster, more complete removal of hydrolyzable chloride impurities than conventional processes.

4 Claims, No Drawings

4,996,351

PROCESS FOR REDUCING THE QUANTITY OF HYDROLYZABLE CHLORIDES IN ISOCYANATES

BACKGROUND OF THE INVENTION

This invention relates to a process for reducing the quantity of hydrolyzable chlorides and other impurities in isocyanate compounds, particularly isocyanate compounds which are prepared in the reaction of an amine with phosgene.

Many isocyanate compounds are commercially prepared by reacting the corresponding amine with phosgene. Although this process proceeds in good yield, it is plagued by the formation of a significant amount of undesired by-products. These by-products, which include tars, unreacted phosgene, HCl, and other chloride-containing species, must be removed from the isocyanate prior to its use. Their presence is undesirable due to the corrosive nature of chlorine, and because chlorine interferes with catalysts which are used in preparing polyurethanes. This removal is commonly done on a commercial scale by refluxing or heat treating the crude isocyanate compound to drive off the volatile impurities.

It is known to add gaseous HCl or other polar gas during the reflux step in order to accelerate the removal of volatile impurities. However, even using these gases, the removal of volatile impurities is not accomplished as rapidly or as completely as desired. In addition, this method requires the use of additional reagents as well as storage equipment and apparatus for metering the gas to the process stream.

Accordingly, it would be desirable to provide a process for reducing the quantity of hydrolyzable chloride impurities in isocyanate compounds, which process more rapidly and effectively accomplishes such removal.

SUMMARY OF THE INVENTION

This invention is such a process. In one aspect, a process for removing volatile impurities from a crude isocyanate compound which is prepared in the phosgenation of a primary amine, comprising heating said crude isocyanate compound to a temperature sufficient to volatilize said volatile impurities in the presence of an acidic material containing a plurality of strong acid groups.

In another aspect, this invention is an improvement in a process for preparing an isocyanate compound which comprises the phosgenation of a primary amine to form a crude isocyanate compound containing volatile hydrolyzable chloride-containing materials and subsequently removing volatile chloride-containing impurities therefrom, the improvement comprising heating said crude isocyanate compound to a temperature sufficient to volatilize the hydrolyzable chloride-containing materials in the presence of an acidic material containing a plurality of strong acid groups for a period of time sufficient to measurably reduce the quantity of hydrolyzable chloride-containing materials therein.

This invention provides a means to obtain an isocyanate compound having a low level of hydrolyzable chloride impurities, and to obtain such low level of impurities in a surprisingly short period of time. The invention therefore provides a way to increase the rate and ease of manufacture and purification of isocyanate compounds. In addition, although polar gases may be used in conjunction with this invention, their use is not necessary, and the costs associated therewith can be avoided.

DETAILED DESCRIPTION OF THE INVENTION

In this invention, a crude isocyanate compound is heated in the presence of a certain acidic material to remove hydrolyzable chloride-containing chlorides therefrom. The isocyanate compound is any organic isocyanate which is formed by the phosgenation of a primary amine compound. Monoisocyanates, and polyisocyanates (including diisocyanates) can be purified according to this invention. The isocyanate compound can be an aliphatic isocyanate, i.e. one in which the isocyanate group(s) is bound to an aliphatic carbon atom, or one in which the isocyanate groups(s) is bound to an aromatic carbon atom (aromatic isocyanate). Of particular interest herein are polyisocyanates which are useful in the production of polyurethanes, polyureas or polyisocyanurates.

Exemplary isocyanate compounds include methyl isocyanate, butyl isocyanate, phenyl isocyanate, toluene monoisocyanate, toluene diisocyanate, diphenylmethane diisocyanate, phenylene diisocyanate, hexamethylene diisocyanate, tetramethylene diisocyanate, hexahydrotolulene diisocyanate, naphthylene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl -4,4 '-diphenyl diisocyanate, 3,3'-dimethyldiphenylpropane-4,4'-diisocyanate, isophorone diisocyanate, 2-isocyanato-2-(p-isopropenylphenyl)propane, tetramethylxylenediisocyanate, as well as hydrogenated derivatives of the aforementioned aromatic isocyanates.

A crude isocyanate compound is purified according to this invention. A crude mixture, for the purposes of this invention, is that mixture obtained in the reaction of a primary amine and phosgene prior to the removal of undesired by-products. It may include any organic solvent which may be used in the phosgenation step. Such by-products include phosgene, HCl, tars, amine hydrochlorides, and other chlorine-containing impurities. The chlorine-containing impurities include species such as, for example, R—N—N=C(Cl)—N(COCl)—R, R—N(-H)—COCl, R—N=CCl$_2$, and the like, wherein R represents the organic portion of the primary amine compound which has been phosgenated.

The phosgenation of the primary amine compound can be carried out any convenient manner, including described in U. S. Pat. Nos. 3,781,320 and 3,188,337, incorporated herein be reference. The reaction proceeds according to the equation:

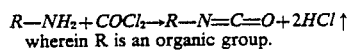
wherein R is an organic group.

The crude isocyanate compound is purified according to this invention by heating it in the presence of a solid or supported material containing a plurality of strong acid groups. The crude compound is heated in the presence of this acidic material to a temperature at or below the boiling and decomposition points of the isocyanate compound but sufficient to volatilize hydrolyzable chloride-containing impurities. If a solvent is present, the temperature is also at or below the boiling point of the solvent. The precise temperature employed will depend on a number of factors which are easily ascertained by those skilled in the art, such as the particular isocyanate compound being treated, its boiling or decomposition temperature, the type of any solvent which may be present and the like. However, a temperature from about 150°–300°, preferably about 180°–220°, more preferably about 185°–200° C. is suitable in most cases. Within the preferred and more preferred temperature ranges, the decomposition and volatilization of chlorine-containing impurities proceed at a commercially acceptable rate while minimizing the energy consumption.

During this heating, the volatile impurities are driven off, thereby reducing the quantity thereof remaining in the isocyanate compound. Although this invention is not limited to any theory, it is believed that in addition, the acidic material promotes the dehydrochlorination and/or oxidation of impurities such as, for example, R—N=C(Cl)—N(COCl)—R, R—N(H)—COCl, RN—N=CCl$_2$, and the like to recover the desired isocyanate and generate HCl and phosgene, which are driven off with the other volatile impurities.

The acidic material used in this invention is any solid or supported material which contains a plurality of strong acid groups and which does not rapidly degrade or undesirably react with the crude isocyanate compound under the conditions at which the purification is conducted. By "strong acid groups", it is meant acid groups having a pKa of $\leq 2$, preferably $<1.5$. Particularly suitable acidic materials include zeolites or artificial zeolites which contain a strong acid functionality, and especially organic polymers containing strong acid groups. It is preferred that the acidic material is a solid which is not soluble in the crude isocyanate compound, so that it can be easily separated from the isocyanate after the hydrolyzable chlorides are removed.

Suitable organic polymers include those containing sulfonic acid moieties attached to a polymer matrix. The polymer matrix may be linear or crosslinked, but if it is linear, it is preferably of a high enough molecular weight so it is insoluble in the crude isocyanate compound and infusible at the temperature of the purification step. The organic polymer also advantageously has a cation exchange capacity of about 0.25 meq/g or more, preferably about 0.9 meq/g or more. Sulfonic acid-type ion exchange resins, which contain a plurality of sulfonic acid moieties pendant from a crosslinked addition polymer, are suitable. Of these, the macroporous or gel-type sulfonated styrene-divinylbenzene resins are of particular note. Such resins are described, for example, in U.S. Pat. Nos. 4,431,785, 4,419,245, 4,256,840, 4,209,592 and 4,478,695, incorporated herein by reference. In addition, linear and crosslinked fluorocarbon sulfonic acid polymers such as described in U.S. Pat. Nos. 3,684,747, 3,849,243, 3,784,747 and 3,257,334, all incorporated herein by reference, are suitable. These latter polymers are preferred due to their resistance to degradation under the conditions encountered in the purification, and their ability to be coated onto various substrates, such as the packing of a distillation column.

The acidic material is contacted with the crude isocyanate compound as it is heated to remove volatile impurities. This is advantageously done in a distillation tower under conditions such that the crude isocyanate is refluxed. Substantially anhydrous conditions are preferred, especially when a fluorocarbon sulfonic acid polymer is used. Such apparatus advantageously contains a packing to increase the effective surface area of the apparatus and therefore increase its efficiency. The acidic material can be immersed in the liquid crude isocyanate at the bottom of the distillation apparatus, or if the crude isocyanate compound is refluxed, it can be suspended above the liquid isocyanate where the vaporous components thereof will contact the resin.

In an especially preferred embodiment, the resin is coated onto or forms part of the packing of the distillation apparatus. The resin can be readily coated onto most common solid packing materials by casting a solution, emulsion or dispersion of the polymer onto the packing and subsequently heating to fuse the polymer onto the substrate. Alternatively, it can be applied by contacting the molten polymer to the packing material.

The crude isocyanate compound is contacted with the acidic material and heated for a sufficient period of time to reduce the quantity of hydrolyzable chlorides contained therein to a desired level. The precise time required depends on a number of factors, including the initial and desired final level of hydrolyzable chlorides, the particular isocyanate being manufactured, the temperature at which the heating is conducted, the amount of isocyanate being treated, the rate of such treatment, and the like. However, in the usual case where it is desired to reduce the level of hydrolyzable chlorides to less than about 1500, preferably less than about 1000, more preferably less than about 500 ppm, most preferably less than about 200 ppm, a contact time of about 0.5 to about 120 minutes, preferably about 1–90 minutes, more preferably about 3 to about 15 minutes, is usually sufficient. The preferred and more preferred times more closely reflect economically feasible and technically sufficient contact times in a commercial scale operation.

Although not required in this invention, an inert gas may be contacted with the crude isocyanate during the heating step to further aid in removing gaseous impurities. Inert gases are those which do not undesirably react with the crude isocyanate. Suitable gases include HCl, nitrogen, carbon dioxide, carbon monoxide, argon, and the like. The use of such gases is described, for example, in U.S. Pat. Nos. 3,219,678, 3,549,504, 3,851,871 and 4,193,937, incorporated by reference.

Following the heating and removal of volatile impurities, the crude isocyanate can then be further purified and recovered in any convenient manner. In the usual circumstance where a solvent is present, it is typically distilled from the product isocyanate. The isocyanate is conveniently separated from non-volatile impurities by distillation or other convenient techniques.

The resulting isocyanate compound is useful for a variety of purposes, including the production of pharmaceuticals, polyurethanes, polyureas, polyisocyanurates and the like. Polyurethanes can be prepared according to the the teachings of U.S. Pat. No. 4,246,363, among other methods as are well known in the art.

The following examples are provided to illustrate the invention, but are not intended to limit the scope thereof. All parts and percentages are by weight unless otherwise indicated.

EXAMPLE 1

A quantity of crude toluene diisocyanate (TDI) is obtained from a commercial TDI process stream. This stream contains about 12 wt.-% TDI, 87 wt.-% o-dichlorobenzene as a solvent, and the remainder impurities. A portion of this crude TDI is analyzed for hydrolyzable chloride and found to contain 1406 parts per million (ppm) chlorine. The level of hydrolyzable chlorine is rather low because the sample has previously been refluxed. The refluxed crude TDI is used in this example because the easily strippable chlorine has already been removed, and the effectiveness of the invention in removing the difficultly removed chlorine is more clearly demonstrated.

A 150 g. sample of the crude TDI is placed in a 250 ml flask equipped with a magnetic stirrer and a reflux condenser. The crude TDI is brought to reflux (about 180°-190° C.) and 50 g of coated ceramic beads which are coated with 15 grams of a dried perfluorosulfonic acid resin are added. Upon addition of the resin, the solution foams vigorously. The refluxing of the crude TDI is continued, with samples being removed from the flask periodically to determine the hydrolyzable chloride content. Results are as indicated as Sample No. 1 in Table 1 following.

For comparison, a sample of refluxed crude TDI containing 1759 ppm of hydrolyzable chloride is refluxed in identical manner, except no acidic organic resin is added. The results are as indicated as Comparative Sample A in Table 1.

Also for comparison, a sample of refluxed crude TDI containing 1691 ppm of hydrolyzable chloride is refluxed in identical manner, except 95 ml/min (STP) of nitrogen is added to the crude TDI by means of a medium porosity glass frit located below the surface of the refluxing liquid. The results are as indicated as Comparative Sample B in Table 1 following.

TABLE 1

| Time, min. | Hydrolyzable Chloride, ppm | | |
|---|---|---|---|
| | Sample No. 1 | Comp. Samp. A* | Comp. Samp. B* |
| 0 | 1406 | 1759 | 1691 |
| 5 | 490 | N.D. | 866 |
| 30 | 173 | 332 | 419 |
| 60 | 76 | 163 | N.D. |
| 90 | 23 | N.D. | 65 |
| Overnight | N.D | 55 | N.D. |

N.D. - Not determined
*Not an example of this invention.

The data in Table 1 show the improvement provided by this invention. At any given point in the refluxing process, the process of this invention provides a substantially lower level of hydrolyzable chloride impurities. A particularly striking comparison is between Sample No. 1 and Comparative Sample A. The process of this invention provides a hydrolyzable chloride level after 90 minutes which is lower than obtained with a full night of simple refluxing.

EXAMPLE 2

Comparative Sample No B (in which a $N_2$ purge is used) is repeated, this time adding 50 grams of the coated ceramic beads used in Sample No. 1. The results are as reported as Sample No. 2 in Table 2. As can be seen from this data, excellent reduction of the chlorine content is obtained. Using the sulfonic acid resin in conjnction with a nitrogen purge provides better results than using the sulfonic acid alone. This is surprising since the use of nitrogen alone provides results inferior to when neither nitrogen or the sulfonic acid resin are used.

TABLE 2

| Cl reduction in Sample No. 2 | |
|---|---|
| Time, min. | Hydrolyzable Chlorine, ppm |
| 0 | 1877 |
| 5 | 296 |
| 15 | 220 |
| 30 | 128 |
| 60 | 40 |

EXAMPLE 3

In order to simulate a packed distillation tower containing an acidic material in the packing, a flask is modified to permit the insetion of a 2"steel pallring coated with about 1.5 g of a fluorocarbon sulfonic acid resin. The inserted pallring sits in the crude TDI. In addition, a nitrogen purge of 100 ml/min (STP) is maintained in such a manner that only the headspace is purged. A 320-gram sample of a refluxed crude TDI is added to the flask and heated as in Example 1. The results obtained are as indicated as Sample No. 3 in Table 3 following.

Sample No. 4 is conducted in like manner, except 50 g of small silicon carbide cylinders which are coated with the fluorocarbon sulfonic acide resin are substituted for the coated pallring. The results are as indicated in Table 3 following.

For comparison, Sample No. 3 is repeated without the use of any acidic material These results are reported as Comparative Sample B in Table 3.

TABLE 3

| Time, min. | Hydrolyzable Chlorine, ppm | | |
|---|---|---|---|
| | Sample No. 3 | Sample No. 4 | Comp. Samp. B* |
| 0 | 974 | 502 | 1027 |
| 1 | 435 | 277 | N.D. |
| 5 | 353 | 206 | 461 |
| 15 | 243 | 120 | 365 |
| 30 | 156 | 70 | 198 |

N.D.- Not determined.
*Not an example of this invention.

As can be seen from the data in Example 3, the presence of an acidic material substantially reduced the quantity of hydrolyzable chlorine present at any given point in the heating step. The combined use of the acidic material and nitrogen purge is especially effective, which is surprising since the nitrogen is known not to be helpful in the absence of the resin.

EXAMPLE 4

Sample No 4 is repeated, this time adding a 95 ml/min (STP) HCl purge below the surface of the liquid crude TDI. After 30 minutes refluxing, the hydrolyzable chlorine is reduced from 502 ppm to only 50 ppm.

What is claimed is:

1. A process for removing volatile impurities from a crude isocyanate compound which is prepared in the phosgenation of a primary amine, comprising heating said crude isocyanate compound to a temperature sufficient to volatilize said volatile impurities in the presence of an acidic material containing a plurality of strong acid groups, wherein the acidic material is an organic polymer which is coated onto or forms part of the packing of a distillation apparatus.

2. A process for removing volatile impurities from a crude isocyanate compound which is prepared in the phosgenation of a primary amine, comprising heating said crude isocyanate compound to a temperature sufficient to volatilize said volatile impurities in the presence of an acidic material containing a plurality of strong acid groups, wherein the acidic material is selected from the group consisting of zeolites or artificial zeolites which contain strong acid groups.

3. An improvement in a process for preparing an isocyanate compound by the phosgenation of a primary amine to form a crude isocyanate compound containing volatile hydrolyzable chloride-containing materials, the improvement comprising heating said crude compound to a temperature sufficient to volatilize the hydrolyzable chloride-containing materials in the presence of an acidic material containing a plurality of strong acid groups for a period of time sufficient to measurably reduce the quantity of hydrolyzable chloride-containing materials therein, wherein the acidic material is an organic polymer which is coated onto or forms part of the packing of a distillation apparatus.

4. An improvement in a process for preparing an isocyanate compound by the phosgenation of a primary amine to form a crude isocyanate compound containing volatile hydrolyzable chloride-containing materials, the improvement comprising heating said crude compound to a temperature sufficient to volatilize the hydrolyzable chloride-containing materials in the presence of an acidic material containing a plurality of strong acid groups for a period of time sufficient to measurably reduce the quantity of hydrolyzable chloride-containing materials therein, wherein the acidic material is selected from the group consisting of zeolites or artificial zeolites which contain strong acid groups.

* * * * *